US010966653B2

(12) United States Patent
Santailler

(10) Patent No.: US 10,966,653 B2
(45) Date of Patent: Apr. 6, 2021

(54) ALLERGEN EXPOSURE SYSTEM COMPRISING A CHAMBER FOR MIXING AIR AND ALLERGENS, WHICH IS SEPARATED FROM THE EXPOSURE ROOM THAT ACCOMMODATES THE PATIENTS

(71) Applicant: ALYATEC, Strasbourg (FR)

(72) Inventor: Gérard Santailler, Marcy (FR)

(73) Assignee: ALYATEC, Strasbourg (FR)

( * ) Notice: Subject to any disclaimer, the term of this patent is extended or adjusted under 35 U.S.C. 154(b) by 419 days.

(21) Appl. No.: 15/120,407

(22) PCT Filed: Feb. 16, 2015

(86) PCT No.: PCT/FR2015/050366
§ 371 (c)(1),
(2) Date: Aug. 19, 2016

(87) PCT Pub. No.: WO2015/132497
PCT Pub. Date: Sep. 11, 2015

(65) Prior Publication Data
US 2017/0065219 A1 Mar. 9, 2017

(30) Foreign Application Priority Data

Mar. 3, 2014 (FR) ....................................... 1451669

(51) Int. Cl.
*A61B 5/00* (2006.01)
*A61M 11/06* (2006.01)
(Continued)

(52) U.S. Cl.
CPC ............ *A61B 5/411* (2013.01); *A61B 5/6888* (2013.01); *A61G 10/02* (2013.01); *A61M 11/003* (2014.02);
(Continued)

(58) Field of Classification Search
None
See application file for complete search history.

(56) References Cited

FOREIGN PATENT DOCUMENTS

EP 1335750 A2 8/2003
JP 2010063967 A * 3/2010
(Continued)

OTHER PUBLICATIONS

Machine translation of JP-2010063967-A (Year: 2010).*
(Continued)

*Primary Examiner* — Patrick Fernandes
*Assistant Examiner* — Benjamin S Melhus
(74) *Attorney, Agent, or Firm* — Marshall, Gerstein & Borun LLP

(57) ABSTRACT

An allergen exposure system includes a mixing chamber, delimited by walls and distinct from the air inlet duct and from the exposure room in which the patients are situated. A mixing between a stream of allergen particles from an allergen injection device and a flow of air devoid of allergens which has passed through a filtration device, occurs through a phenomenon of microturbulence in this mixing chamber which forms a widening with respect to the air inlet duct and makes it possible to obtain a flow of air laden with allergen particles which is injected into the exposure room through at least one diffusion outlet so that it can be inhaled by the patients. This invention is of benefit to medical and pharmaceutical research in the field of allergy study.

20 Claims, 5 Drawing Sheets

(51) Int. Cl.
*A61G 10/02* (2006.01)
*A61M 11/02* (2006.01)
*A61M 11/00* (2006.01)
*A61M 16/00* (2006.01)

(52) U.S. Cl.
CPC ............ *A61M 11/02* (2013.01); *A61M 11/06* (2013.01); *A61M 16/0066* (2013.01); *A61M 2202/064* (2013.01); *A61M 2205/3306* (2013.01); *A61M 2205/3368* (2013.01); *A61M 2205/75* (2013.01); *A61M 2205/84* (2013.01); *A61M 2206/14* (2013.01)

(56) References Cited

FOREIGN PATENT DOCUMENTS

WO    WO-2007/140601 A1    12/2007
WO    WO-2010/0063714 A1    6/2010

OTHER PUBLICATIONS

Day et al., The role of allergen challenge chambers in the evaluation of anti-allergic medication: an international consensus paper, Clin. Exp. Allergy Rev., 6(2):31-59 (2006).

Eduard et al., Generation and homogeneity of aerosols in a human whole-body inhalation chamber, Ann. Occupational Hygiene, 52(6):545-54 (2008).

International Search Report, International Application No. PCT/FR2015/050366, dated Jun. 5, 2015.

Le Brun et al., A review of the technical aspects of drug nebulization, Pharm. World Sci., 22(3):75-81 (2000).

Lidén et al., A new whole-body exposure chamber for human skin and lung challenge experiments—the generation of wheat flour aerosols, Ann. Occup. Hyg., 42(8):541-7 (1998).

Monséet al., Considerations for the design and technical setup of a human whole-body exposure chamber, Inhal. Toxicol., 24(2):99-108 (2012).

\* cited by examiner

ALLERGEN EXPOSURE SYSTEM COMPRISING A CHAMBER FOR MIXING AIR AND ALLERGENS, WHICH IS SEPARATED FROM THE EXPOSURE ROOM THAT ACCOMMODATES THE PATIENTS

CROSS-REFERENCE TO RELATED APPLICATIONS

This application is a national stage application under 35 U.S.C. § 371 and claims the benefit of priority of international application no. PCT/FR2015/050366, filed Feb. 16, 2015, which claims the benefit of priority under 35 U.S.C. §. 119 of French patent application no. 1451669, filed Mar. 3, 2014, the entire contents of each being hereby incorporated herein by reference, in its entirety and for all purposes.

TECHNOLOGICAL FIELD

This present disclosure concerns an allergen exposure system comprising an exposure room intended to accommodate patients and in which an inhalation atmosphere with a controlled allergen content is generated in order to provoke an allergic reaction among these patients.

The exposure room is a confined chamber of the EEC type (standing for Environmental Exposure Chamber or European Exposure Chamber), and also known as an allergy test chamber.

BACKGROUND

Allergies are a global scourge, affecting more than one out of four people in the western world. It is believed that within the next few years, almost 50% of the population of the developed countries may be affected by at least one allergenic illness. Medical research in the field of allergies, and especially in the development of anti-allergic medication or desensitizing treatment, is accordingly a fast-growing sector.

To carry out clinical trials concerning allergies, or to assess the efficiency of new drugs or desensitization treatment, observing the reaction of allergic patients when they are exposed to natural allergens is essential.

Making observations like this in the natural environment, scientifically and objectively, is particularly difficult because of the major changes in the quantity of allergens that a patient inhales, depending, for instance, on the season, the weather conditions or the places frequented by the patient. Indeed, the quantity of allergens occurring naturally in ambient air varies enormously according to, for instance, the area or the season, the weather conditions, especially temperature, humidity or the presence of winds, the time of the day, or even the elevation with respect to ground level.

To be able to overcome the many parameters that fluctuate in a way that is difficult to control, in prior art, devices known as allergy test chambers or EECs (European/Environmental Exposure Chamber) have been developed.

These devices accommodate one or several patients in a closed environment where a controlled amount of allergens is released, to observe scientifically their physiological reaction after a longer or shorter exposure period. The various experimental parameters used in the chamber are constant and controlled throughout the experiment. Accordingly, trials can be performed under reproducible conditions on several patients or several times on the same patient and results that are comparable with one another can be immediately obtained in a reliable way.

Such devices allow allergenic inhalation tests to be carried out under controlled conditions close to the natural state, and that are reproducible. They guarantee reliable, complete, and comparable results that can be used scientifically as part of many clinical studies. For instance, they can be used for in vivo testing of the efficiency of desensitization treatment or of new anti-allergenic medications and, for instance, to determine the doses to be prescribed, or the efficiency time.

For instance, an allergy test chamber described in the European patent No. EP 1335750 by HORAK or those described in the patent applications FRAUNHOFER WO 2010/0063714 and PATEL WO 2007/140601 are known.

In these known prior devices, one constant concern relates to obtaining a homogeneous concentration of allergens throughout the exposure room. Indeed, for the results to be reliable and usable, it is particularly important to make sure that the patients are exposed to the same allergen concentration, wherever they are located in the room. Therefore, in the prior art, various devices for distributing and diffusing allergens in the exposure room have been imagined.

In the HORAK patent, on the one hand an allergenic powder is infed via a compressed air particle dispenser in the ceiling of the exposure room and on the other, fresh air devoid of allergens via spherical nozzles, separate from the particle dispenser, also ceiling-mounted but at different places and pointing in different directions in order to generate a turbulent air flow.

In the FRAUNHOFER and PATEL patents, a liquid preparation of allergens is used from which an aerosol is generated. Once this aerosol is fed into the exposure room, one or several fans mixes it with the ambient air in the exposure room coming from separate air inlets.

In all these devices, the air and the allergen particles are mixed directly in the exposure room by means of a strong turbulent air flow or by fans.

Distribution systems like this are not satisfactory and do not guarantee uniform mixing and homogeneous concentration throughout the entire exposure room when such a room is large. The concentration differs depending on the height from the floor level and the distance from the inlet zone of the allergens or the position with respect to the fans.

In addition, high turbulences and strong air flows generated by the nozzles and/or fans are disagreeable to patients in the exposure room, also liable to cause the degradation of the allergens which consist of particularly fragile compounds or a rearrangement of particles by an aggregation changing their size.

The following publications are also known: W. EDUARD AND AL. "Generation and Homogeneity of Aerosol in a Human Whole-Body Inhalation Chamber", C. LINDEN AND AL. "New Whole-body Exposure Chamber for Human Skin and Lung Challenge Experiments—the Generation of Wheat Flour Aerosol" and CHRISTIAN MONSE AND AL. "Considerations for the design and technical set-up of a human whole-body exposure chamber".

These documents describe the respective exposure systems for aluminium oxide, wheat flour and gases. In these systems, mixing with the ventilation air no longer takes place in the exposure room but upstream of it, directly in the air inlet duct, whether it concerns a coaxial internal duct opening out longitudinally into the air duct as in the first document, or via a simple T connection as described in the two other documents.

The mixture obtained with these prior devices is not satisfactory either, because the flow of air circulates too fast through the inlet duct for real mixing to take place. The particles are simply drawn in by a Venturi effect and carried without there being any real mixing between the various flows.

SUMMARY

The device according to the presently described embodiments, to the contrary, guarantees a far better mixture between the air and the allergen particles, producing far higher homogenizing of the concentration of allergens throughout the entire exposure room and with far less risk of damaging the allergen particles.

To do this, the presently described embodiments comprise an allergen exposure system comprising an allergen injection device, an air inlet duct and an exposure room containing the air charged with allergen particles obtained by mixing a flow of allergen particles from the allergen injection device and a flow of air devoid of allergens fed in through the air inlet duct, this exposure room being designed to accommodate patients inhaling the air containing allergen particles to cause an allergic provocation.

According to the presently described embodiments, the allergen exposure system also comprises a mixing chamber, contained by walls, separate from the air inlet duct and the exposure room, in which occurs said mixture between the flow of allergen particles and the flow of air devoid of allergens.

This mixing chamber, upstream of the exposure room, is a hollow volume enclosed by walls whose shape and composition are adapted to avoid any risk of deterioration to the allergen particles.

It comprises at least one first inlet, known as the allergen inlet, connected with the allergen injection device output and through which the flow of allergen particles enters, preferably in the form of a fine nebulized mist. This first inlet is adapted so as not to degrade the allergens passing through it. For instance, it does not comprise nozzles or an aggressive system liable to damage the allergens. Preferably, it comprises a set of one or several simple openings. Preferably, this inlet connects directly or by means of a short straight duct to the outlet of the allergen injection device. The mixing chamber also includes at least one second inlet, known as the air inlet, connected to the air inlet duct and through which the flow of air devoid of allergens intended to ventilate the exposure room penetrates. This second inlet is preferably equipped with a filtration device, preferably a high efficiency filtration system, to guarantee that the air entering the mixing chamber is devoid of allergens other than those deliberately fed in through the first inlet.

Finally, the mixing chamber comprises at least one diffusion outlet connected to the exposure room and through which a flow of air containing allergen particles, obtained by mixing the flow of air devoid of allergens and the flow of allergen particles in the mixing chamber, escapes towards the exposure room. Preferably, this consists of an opening made in the wall of the mixing chamber, opening into the exposure room or into an open duct extending from the mixing chamber to the exposure room.

Near the air inlet, the mixing chamber has a widening with respect to the air inlet duct causing an expansion of the flow of air devoid of allergens when it enters the chamber.

Accordingly, the speed of the air is slowed down when it enters the mixing chamber and only low intensity micro-turbulences are created. In this way, more efficient mixing of the flow of air with the flow of allergen particles is obtained, giving them the time to inter-penetrate and mix thoroughly before reaching the diffusion outlet.

This mixture is also far gentler, limiting the risks of damaging the fragile allergen particles and causing very little rearrangement of the particles by aggregation, often encountered in the prior devices with extensive mixing or turbulences. The size of the particles inhaled by the patients in the exposure room is far more stable and consistent, allowing it to be better controlled.

Near the diffusion outlet, the section of the mixing chamber may preferably decrease in order to form a narrowing section.

The flow of air containing the allergen particles is therefore accelerated by compression just before its outlet from the mixing chamber. Accordingly, it enters the exposure room at a sufficiently high speed to guarantee the carrying of all the allergen particles into the entirety of the exposure room.

In the mixing chamber, the first inlet and the second inlet can be arranged advantageously with respect to one another so that the air entering trough the second inlet sweeps the first inlet thus drawing with it any allergen particles entering through the first inlet and creating micro-turbulences in the mixing chamber to ensure excellent mixing between the two flows and guarantee outlet through the at least one diffusion outlet of a flow of air containing allergen particles that is homogeneous and of a substantially constant concentration.

According to an embodiment, the first inlet and the second inlet of the mixing chamber are placed substantially perpendicular to one another.

According to an embodiment, the allergen injection device is a nebulizer, more preferentially a capillary wave atomizer, and the flow of allergen particles forms a nebulisate.

According to one embodiment, the mixing chamber may also have a gradual narrowing following by a gradual widening of its width, thus forming a throttle zone in which the allergen inlet is located.

According to one embodiment, the mixing chamber may be situated, at least partially, above the exposure room.

Thanks to the mixing chamber, an excellent mixture is obtained between the two flows and the concentration of allergens in the resulting flow leaving the mixing chamber and entering the exposure room is controlled. The mixture is outstanding, without any risk of degradation of the allergens and turbulences, limited to micro-turbulences, are situated inside the mixing chamber thus considerably improving the comfort of the patients in the exposure room.

Depending on the size and shape of the exposure room, the mixing chamber has a suitable number of diffusion outlets arranged to guarantee homogeneous diffusion of the air containing the allergens into the exposure room, without any preferential direction.

BRIEF DESCRIPTION OF THE FIGURES

Other characteristics and advantages will be revealed by reading the detailed description that follows, referring to the attached illustrations, in which.

DETAILED DESCRIPTION

The allergen exposure system is now described in detail with reference to the FIGS. 1 to 7. The equivalent components shown in the various figures will bear the same numerical references.

Figure 1:
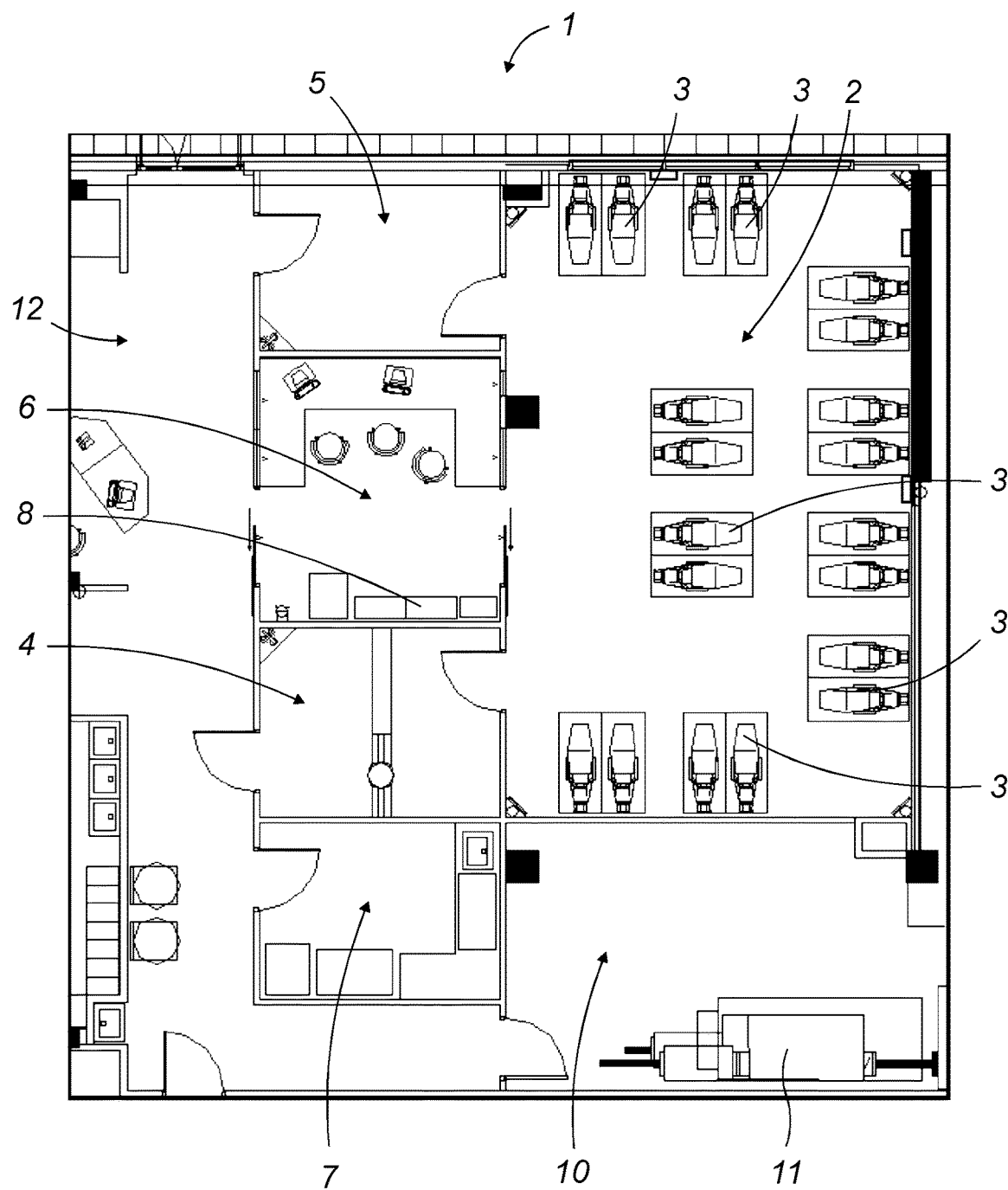
FIG. 1 is a general schematic top view of an example of the allergen exposure system.
Figure 2:
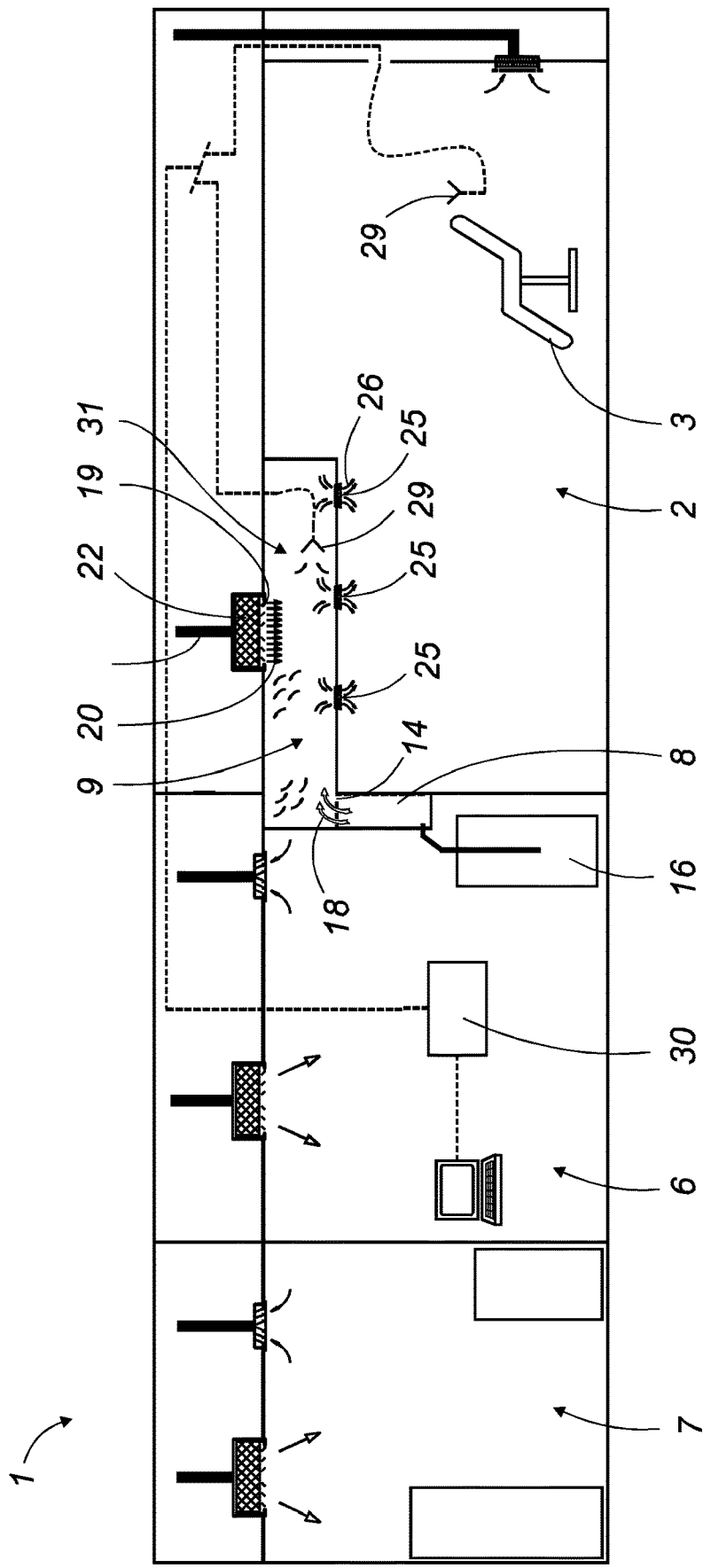
FIG. 2 is a schematic transverse cross view of an example of the allergen exposure system vention.
Figure 3:
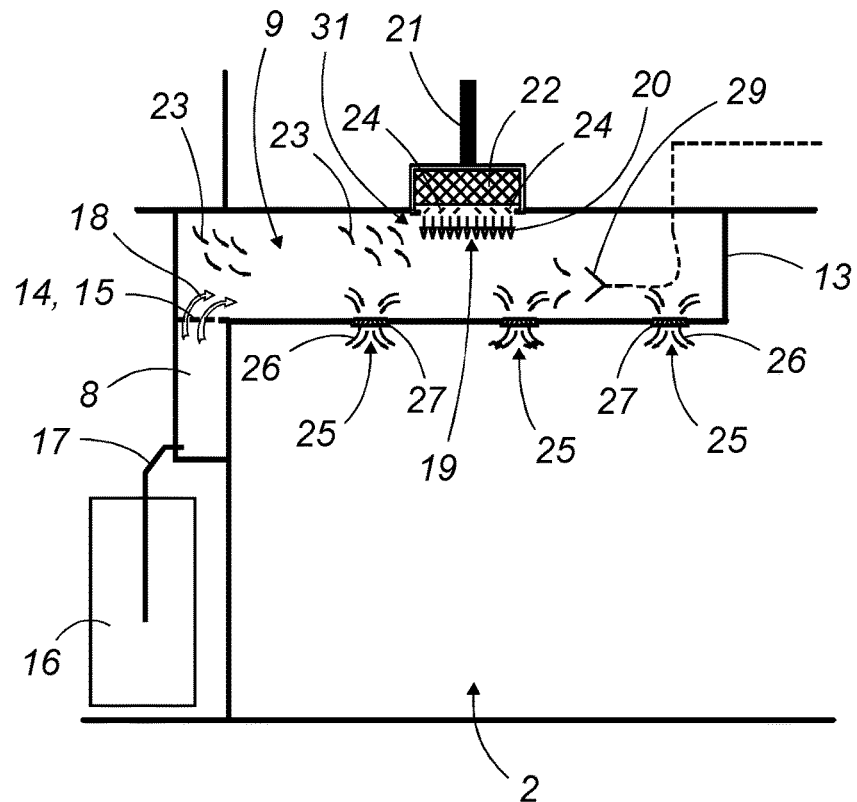
FIG. 3 is a schematic cross view of an example of the mixing chamber for an allergen exposure system.

FIG. 1 depicts the general plan of an example of the allergen exposure system 1, comprising several rooms.

The allergen exposure system 1 comprises an exposure room 2 designed to accommodate the patients to be observed and in which the controlled allergen content inhalation atmosphere can be produced.

The exposure room 2 is a confined chamber where the ambient pressure is lower than the reference pressure (that of the rooms surrounding the exposure system 1) and than the remainder of the exposure system 1.

The size and shape of the exposure room 2 depend on the system location, the technical requirements to be complied with and what the operators want.

Figure 5:
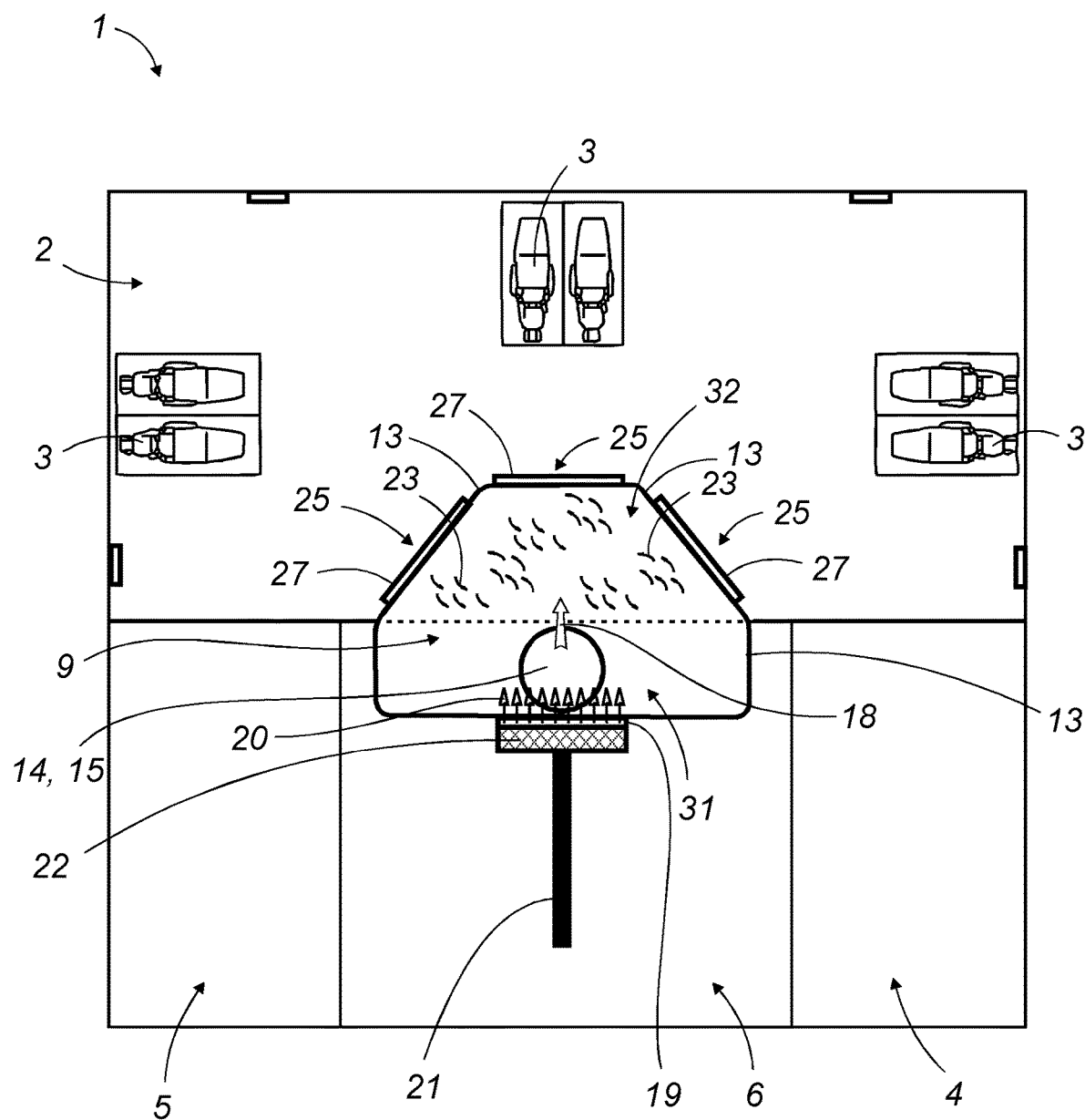
FIG. 5 is a top view of an example of the mixing chamber and exposure room corresponding to that of FIG. 4 for an allergen exposure system.

It contains one or several chairs 3 where the patients can sit comfortably for the entire exposure period. As a non-limitative example, the exposure room 2 shown in FIG. 1 comprises twenty chairs 3 set out in groups of two throughout the room while the room shown in FIG. 5 is smaller, comprising only six chairs 3.

An entrance airlock 4 and an exit airlock 5, at a higher pressure than the exposure room 2 and the outside, enables the patients to enter and exit the exposure room 2 without any contamination by allergens outside the allergen exposure system 1. These airlocks 4 and 5 also prevent outside pollutants (other allergens, chemical compounds) from entering into the exposure room 2.

A control room 6, also at a higher pressure than exposure room 2 and the outside, enables operators to enter and adjust or check the various experiment parameters and monitor the patients occupying exposure room 2.

The allergen composition intended to be inhaled by the patients is prepared, for instance, in a laboratory 7 equipped for its preparation while offering the technicians and patients total safety. The composition is then placed in an allergen injection device 8 which feeds it into a mixing chamber 9, not shown in the FIG. 1, but which will be extensively described below, with reference to the following figures.

The allergen exposure system 1 may also comprise a technical room 10 containing, for instance the devices 11 required for ventilation, humidification, air-conditioning and/or heating the various rooms of the allergen exposure system 1 or any other apparatus or bulky equipment required for the operation of system 1.

The system can be completed by a reception and waiting room 12 for the patients.

According to the described embodiments, the allergen exposure system 1 comprises a mixing chamber 9 of which several examples are shown in the FIGS. 2 to 7.

It concerns a hollow volume, contained by walls 13 forming a box, which is distinct and separate from the exposure room 2 and also distinct and separate from the air inlet duct, in which the allergen particles are mixed with a flow of air devoid of allergens, before being fed into the exposure room 2.

In order not to damage the allergen particles and to facilitate cleaning between two exposure sessions, the walls 13 of mixing chamber 9 are preferentially smooth, without any aggressive protruding parts or sharp angles or corners liable to allow matter accumulation.

Preferably, they will be made of a material which does not release or releases few particles and volatile organic compounds (VOCs), and that are easily cleaned and resist the products used for cleaning (for instance $H_2O_2$). For the purpose, it would be possible to use, for instance, thermosetting high pressure laminated (HPL) panels, such as compact blocks, for instance, and in particular those sold under the name FUNDERMAX® or ATHLON®. These are a material consisting of paper-based composites impregnated with phenol resin and melamine resin, fireproofed in the mass. For instance, it would also be possible to use an acrylic resin with mineral fillers, in particular as marketed under the names CORIAN®, HI-MAX® or STARON®.

In the patent application, a "material which releases few particles" will be defined as a material releasing a number of particles less than that required to obtain an ISO rating less than or equal to 7 according to standard 14644-1.

The mixing chamber 9 comprises at least one inlet, called the allergen inlet 14, through which the allergen particles to be inhaled by the patients are infed.

Figure 7:
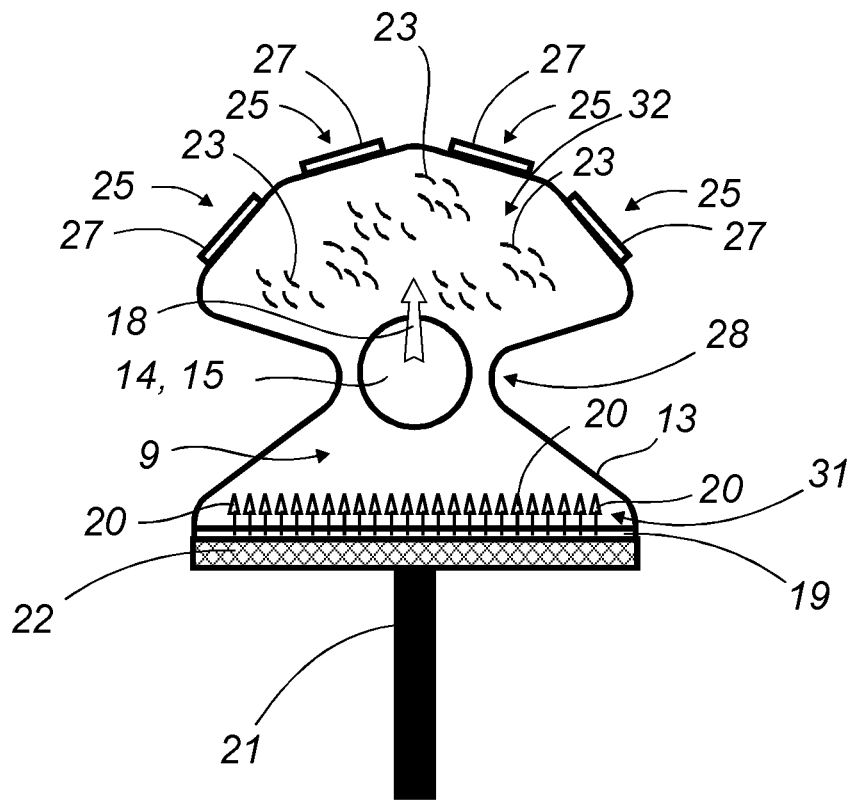

This allergen inlet 14 is adapted so as not to degrade the allergens passing through it. It does not comprise nozzles or an aggressive system liable to damage the allergens. In particular, it may be a simple opening 15, for instance circular, as shown in FIGS. 5 and 7.

The allergen inlet 14 is connected to the outlet of the allergen injection device 8, preferably directly as shown, or for instance, by means of a short straight duct.

Naturally, other forms of connection, less favourable to the preservation of the integrity of the allergen particles are possible, in particular a bent or longer inlet duct.

Figure 6:
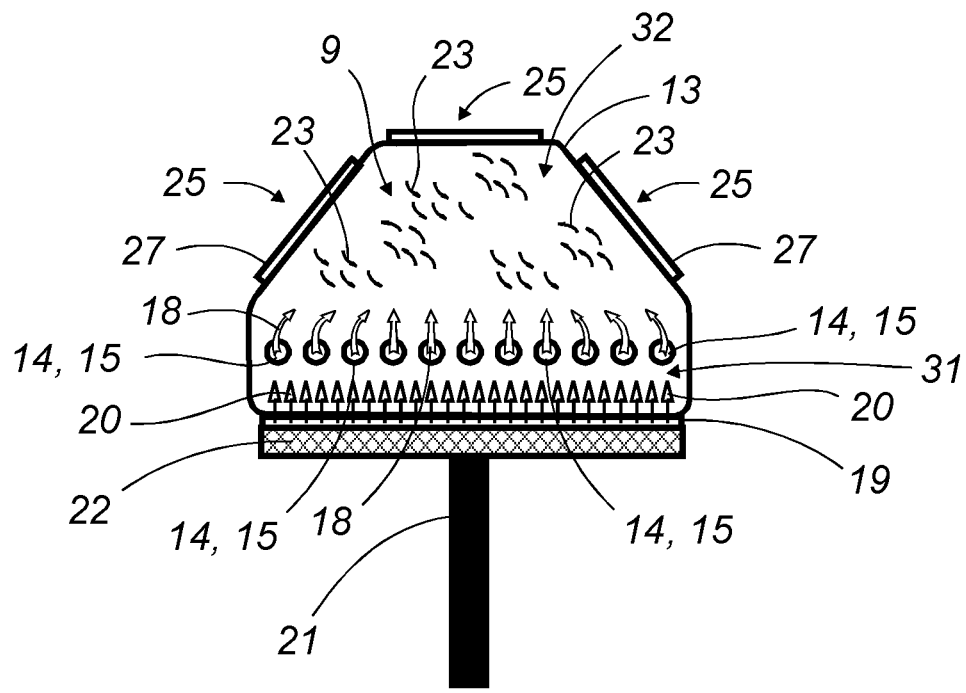
FIGS. 6 and 7 are top views of two other examples of the mixing chamber.

According to another embodiment, the mixing chamber may comprise several allergen inlets 14, for instance in the form of a set of openings 15, substantially aligned like an injection pipe as shown in the example of FIG. 6. Other arrangements of these allergen inlets 14 are obviously possible without moving out of the scope of this described embodiments.

The allergen injection device 8 can be of any type depending on the techniques that the operator wishes to use. It may consist of a pneumatic allergen powder injection device or preferably of an injection device operating from a liquid composition of allergens, such as a spray, an atomizer or a nebulizer, for instance.

In a preferred embodiment, the allergen injection device 8 is a capillary wave atomizer.

In the examples shown, the liquid allergen composition prepared in the laboratory 7 is poured into a tank 16 then fed into the allergen injection device 8 by duct 17. It is then injected into the mixing chamber 9 into which it penetrates through the opening or openings 15 forming the allergen inlet 14 (inlet phenomenon).

In the figures, the flow of allergen particles 18 is symbolized by white arrows. Preferably, it concerns a fine nebulized mist.

The mixing chamber also comprises at least one air inlet 19 through which arrives the air devoid of allergens designed to ventilate the exposure room 2. This flow of air 20, laminar and devoid of allergens, is symbolized in the figures by black arrows with a white tip.

This air inlet 19 is connected to an air inlet duct 21.

Preferably, a filtration device 22 is arranged at the air inlet 19 or interposed between this air inlet 19 and the air inlet duct 21, to prevent any allergens or other unwanted particles, and possibly even some chemical pollutants, present in the air entering through the air inlet duct 21, from penetrating into the mixing chamber 9 and subsequently into the exposure room 2.

The filtration device 22 operates in both directions, guaranteeing among other things that the allergen particles in the mixing chamber 9 are unable to leave via the air inlet duct 21 in the event of the flow of air being cut off. Retro-contamination is thus avoided and the containment of the exposure room 2 is ensured.

The filtration device 22 preferably comprises a high efficiency filtration device, also known as a HEPA filter (High Efficiency Particulate Air filter), or an ultra high efficiency filtration device, known as an ULPA filter (Ultra Low Particulate/Penetration Air filter), as defined in the standard EN 1822-1. Among these, it is advantageous to choose a filter of the H14 type, preferably completed by one or several filters active against VOCs (volatile organic compounds), for instance based on activated carbon, cold plasma, porous ceramics or other means.

An HEPA filter of the H14 type offers the advantage of being an absolute filter which can be qualified prior to the use of the allergen exposure system 1 by an integrity test according to the standard 14644-3.

Preferably, the filtration device 22 has an insertable filter case which is preferably inserted into the air inlet 19 of the mixing chamber 9 and which, for instance, is in the form of a thick plate or a rectangular or round cartridge, or of any other appropriate shape.

According to another non-limitative alternative, the filtration device 22 can also include, instead of or in addition to the insertable case, a filter case in a duct, located inside the air inlet duct 21, although it is less easy for cleaning.

The size of the filtration device 22, in particular the filtering surface, obviously depends on the low rate of the incoming flow of air 20 and therefore on the volume of the exposure room 2 to be a ventilated. Indeed, the flow rate of the flow of air 20 must be proportional to the volume of the exposure room 2 to guarantee a satisfactory mixing level in the exposure room, preferably conforming to the standard 14644-1 so that a particle classification without exposure of ISO8 class can be obtained for the exposure room 2.

For a small exposure room 2 as shown in FIG. 5, a small filtration device 22 will be sufficient whereas a more widely-encompassing filtration device 22, as in the examples of FIGS. 6 and 7, will be necessary for a large exposure room 2, in particular the one shown in FIG. 1.

In the mixing chamber 9, the flow of air 20 entering through the air inlet 19 reaches an inlet zone having a larger section than that of the air inlet duct 21. It thus forms a widening 31 compared to this air inlet duct 21, causing pressure reduction by the expansion of the flow of air 20 devoid of allergens when it enters the chamber. Therefore the speed of the flow of air 20 is slowed down.

The slowed down flow of air 20 then carries the flow of allergen particles 18 which arrives through the allergen inlet(s) 14.

The outlet pressure of the flow of allergen particles 18 is preferably designed to be higher than the outlet pressure of the flow of air 20 to prevent the air from entering into the allergen injection device 8, although the volume of air entering the mixing chamber 9 is however far greater than that of the allergen particles.

Because of the relative disposition of the air inlets 19 and allergen inlets 14, the shape and limited size of the mixing chamber 9, the pressurizing of the mixing chamber 9 by the incoming flow of air 20, and the reduction of the speed of the flow of air 20 at its inlet into the mixing chamber, micro-turbulences 23, symbolized in the figures by small black arrows, are created in this mixing chamber 9. These micro-turbulences allow gentle and satisfactory mixing of the flow of allergen particles 18 with the flow of air 20, without there being any need to add a mixing device, such as a fan or another device.

To improve this mixing even more, several optional arrangements of the mixing chamber can be imagined by a man skilled in the art.

For instance, the relative disposition of the air inlet 19 and the allergen inlet 14 can be chosen so that the flow of air 20 entering the mixing chamber 9 through the air inlet 19 sweeps over the allergen inlet 14 to carry the flow of allergen particles 18 entering mixing chamber 9 through the allergen inlet 14.

According to an embodiment, the air inlet 19 and the allergen inlet 14, for this purpose, are arranged near one another and substantially perpendicular to each other, that is, so that the flow of air 20 and of the allergen particles 18, opening respectively from air inlet 19 and allergen inlet 14, are perpendicular to one another.

In addition, fins 24, ribs, walls, baffles or any other adapted channeling or deviating means can be used for directing the flows into the mixing chamber 9 and included in the mixing chamber 9, for instance at the air inlet 19, to improve the formation of the micro-turbulences. However, these devices are preferably chosen and arranged in such a way as not to damage the allergen particles.

Accordingly, in the embodiment shown in FIG. 7, the side walls 13 of the mixing chamber 9 are curved inwards to form a gradual narrowing, followed by gradual widening of the width of mixing chamber 9, forming a throttle zone in which the allergen inlet 14 is located.

The entire flow of air 20 entering the chamber through the filtration device 22, even if the latter has a large surface area, is thus directed to the allergen inlet 14 passing above opening 15 and carrying with it the flow of allergens 18.

In addition, the successive effect of compression caused by the narrowing, followed by the pressure reduction resulting from the subsequent widening, favours the appearance of micro-turbulences 23 in the second part of the mixing chamber 9, improving the thorough mixing of the air and the allergen particles.

According to the described embodiments, the mixing chamber 9 also includes at least one diffusion outlet 25, connected directly or indirectly to the exposure room 2 and used for feeding into the exposure room 2 a flow of air containing allergen particles 26, obtained after mixing in the mixing chamber 9 of the flow of air 20 with the flow of allergen particles 18.

This diffusion outlet 25 can be a simple opening arranged in wall 13 of the mixing chamber 9, opening out directly into the exposure room 2 or into an open duct extending from the mixing chamber 9 to the exposure room 2 if these two zones are at some distance from each other.

It can also be equipped with a grille 27 or any other appropriate device for directing or adjusting the flow of air containing the allergen particles 26 without breaking or damaging the allergen particles.

The number, size, arrangement and orientation of these diffusion outlets 25 depend on the size, the accommodation capacity and the shape of the exposure room 2. The diffusion outlet(s) 25 is (are) arranged to ensure the homogeneous distribution of the flow of air containing allergen particles 26 throughout the entire exposure room 2, without a preferential direction or privileged zone.

In some embodiments, the section of the mixing chamber 9 may preferably decrease in order to form a narrowing 32 just before the diffusion outlet or outlets 25. The flow of air containing allergen particles 26 is therefore accelerated again before penetrating into the exposure room 2 to improve the carrying of the allergen particles throughout the exposure room.

Figure 4:
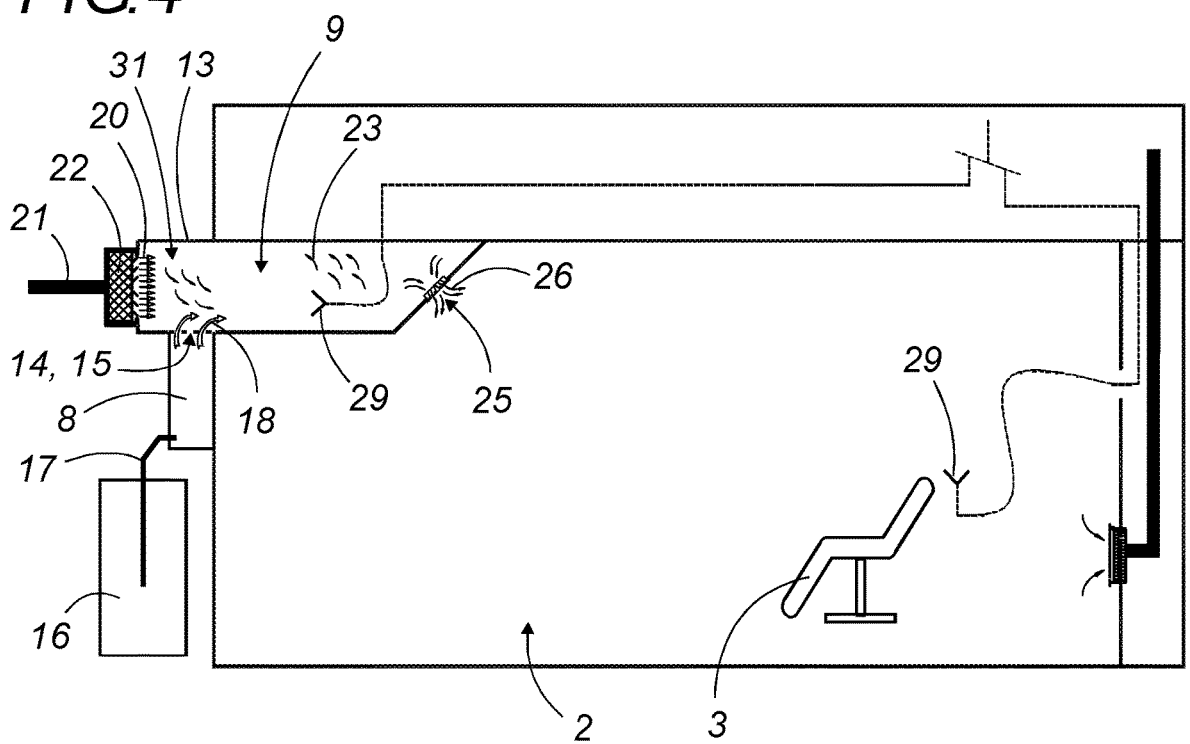
FIG. 4 is a transverse cross view of an example of the mixing chamber and exposure room for an allergen exposure system.

In the example of the embodiment shown in FIGS. 4 and 5, the mixing chamber 9 is situated in a suspended ceiling, partially over the exposure room 2 and, for instance, the control room 6.

Accordingly, it connects directly with the allergen injection device 8 located in the control room 6 through a circular opening 15, opening into the bottom wall of the mixing chamber 9 and which is used as allergen inlet 14.

The air inlet 19 is arranged in the adjacent rear wall of the chamber 9, near the allergen inlet 14, and is directed substantially perpendicularly to it.

The mixing chamber 9 is separated from the exposure room 2 by three portions of wall 13, inclined and oriented in three different directions, in order to face with all the zones of the exposure room 2. It includes three diffusion outlets 25, each located on one of these portions of wall 13, and each of them being directed towards one of the three groups of chairs 3.

The embodiment shown in FIG. 7 includes four diffusion outlets 25, smaller but oriented in four different directions.

According to the application concerned, the man skilled in the art may freely define the number and arrangements most appropriate for diffusion outlets 25, depending on the geometrical parameters of exposure room 2 to be ventilated to guarantee homogeneous diffusion of the air containing allergens in exposure room 2, without there being a preferential direction.

In a preferred embodiment, the mixing chamber 9 may also contain one or several sensors 29 of any appropriate type, such as, for instance, a temperature, pressure or humidity sensor or a sensor connected to a measuring device 30, used for instance, for measuring the concentration or size of the allergen particles, or any other sensor used for monitoring, controlling or guiding the operation of the allergen exposure system 1.

With the allergen exposure system 1, the mixing between the allergen particles and the ventilation air devoid of allergens is not carried out directly in exposure room 2 nor in the air inlet duct 21 but in the mixing chamber 9 which is a separate and distinct place.

Only the flow of air containing the allergen particles penetrates into exposure room 2. This flow is outstandingly homogeneous and can be controlled at the outlet of the mixing chamber 9 by means of one or several sensors 29.

Thanks to the described embodiments, the flow of air inhaled by the patients in the exposure room has the advantage of being very homogeneous with a substantially constant concentration of allergens, with a tolerance of 20% at the most. Such a result cannot be obtained with any of the systems of the prior art.

Obviously, the present description is not confined to the preferential embodiments described previously and shown in the various figures, a man skilled in the art being able to make many modifications and imagine other variants without moving out of the scope or framework defined by the claims.

The invention claimed is:

1. An allergen exposure system comprising:
   an allergen injection device comprising a capillary wave atomizer producing a nebulisate flow of allergen particles;
   an air inlet duct;
   an exposure room containing air containing allergen particles obtained by mixing a nebulisate flow of allergen particles from the allergen injection device and a flow of air devoid of allergens fed in through the air inlet duct, this exposure room being designed to accommodate patients inhaling the air containing allergen particles to cause an allergic provocation;
   a mixing chamber, contained by walls, and separated by the walls from each of the air inlet duct, the allergen injection device, and the exposure room such that each of the air inlet duct, the allergen injection device, and the exposure room is on an opposite side of one of the walls with the mixing chamber, in which mixing chamber occurs a mixture between the flow of allergen particles and the flow of air devoid of allergens;
   the mixing chamber comprises:
   at least one allergen inlet, configured as a first opening in one of said walls, said first opening providing fluid communication between the mixing chamber and an outlet of the allergen injection device and through which the flow of allergen particles penetrates;
   at least one air inlet, configured as a second opening in one of said walls, said second opening providing fluid communication between the mixing chamber and connected to the air inlet duct and through which the flow of air devoid of allergens penetrates;
   at least one diffusion outlet, configured as a third opening in one of said walls, said third opening providing fluid communication between the mixing chamber and the exposure room and through which a flow of air containing allergen particles, obtained by mixing in the mixing chamber the flow of air devoid of allergens and the flow of allergen particles, escapes into toward the exposure room;
   wherein a first area immediately upstream of the air inlet has a first dimension and a second area immediately downstream of the air inlet, in the mixing chamber, has a second dimension greater than the first dimension, causing an expansion of the flow of air devoid of allergens as the flow of air devoid of allergens enters the chamber, and wherein the allergen inlet is situated in the second area.

2. An allergen exposure system according to claim 1, wherein, at an end of the mixing chamber proximate to the diffusion outlet, the section of the mixing chamber decreases to form a narrowing.

3. An allergen exposure system according to claim 1, wherein the at least one diffusion outlet is an opening made in a wall of said walls of the mixing chamber opening out into the exposure room or into an open duct extending from mixing chamber to exposure room.

4. An allergen exposure system according to claim 1, wherein the mixing chamber comprises a gradual narrowing followed by a gradual widening of its width, thus forming a throttle zone in which there is the at least one allergen inlet.

5. An allergen exposure system according to claim 1, wherein air entering the mixing chamber is devoid of allergens other than allergens deliberately introduced through the at least one allergen inlet.

6. An allergen exposure system comprising:
an allergen injection device comprising a capillary wave atomizer producing a nebulisate flow of allergen particles;
an air inlet duct;
an exposure room containing air containing allergen particles obtained by mixing a nebulisate flow of allergen particles from the allergen injection device and a flow of air devoid of allergens fed in through the air inlet duct, this exposure room being designed to accommodate patients inhaling the air containing allergen particles to cause an allergic provocation;
a mixing chamber, contained by walls, and separated by the walls from each of the air inlet duct and the exposure room, in which mixing chamber occurs a mixture between the flow of allergen particles and the flow of air devoid of allergens;
the mixing chamber comprises:
at least one allergen inlet, configured as a first opening in one of said walls, said first opening providing fluid communication between the mixing chamber and an outlet of the allergen injection device and through which the flow of allergen particles penetrates;
at least one air inlet, configured as a second opening in one of said walls, said second opening providing fluid communication between the mixing chamber and connected to the air inlet duct and through which the flow of air devoid of allergens penetrates;
at least one diffusion outlet, configured as a third opening in one of said walls, said third opening providing fluid communication between the mixing chamber and the exposure room and through which a flow of air containing allergen particles, obtained by mixing in the mixing chamber the flow of air devoid of allergens and the flow of allergen particles, escapes into the exposure room;
wherein a first area immediately upstream of the air inlet has a first dimension and a second area immediately downstream of the air inlet, in the mixing chamber, has a second dimension greater than the first dimension, causing an expansion of the flow of air devoid of allergens as the flow of air devoid of allergens enters the chamber, and
wherein the allergen inlet is situated in the second area, at an entrance of the second area, and the allergen inlet is adjacent to the air inlet, and
mixing between the flow of air devoid of allergens coming from the air inlet opening and the allergen particle flow coming from the allergen inlet occurs at the entrance of the second area, adjacent to the air inlet.

7. An allergen exposure system according to claim 6, wherein at least one allergen inlet and at least one air inlet of the mixing chamber are arranged with respect to one another so that the flow of air devoid of allergens penetrating into the mixing chamber through at least one air inlet sweeps said at least one allergen inlet opening to carry the flow of allergen particles that penetrates into the mixing chamber through said at least one allergen inlet.

8. An allergen exposure system according to claim 6, wherein the at least one allergen inlet and the at least one air inlet of the mixing chamber are arranged proximate to one another and substantially perpendicularly with respect to each other.

9. An allergen exposure system according to claim 6, wherein the at least one allergen inlet is connected to the outlet of the allergen injection device directly or by a short straight duct.

10. An allergen exposure system according to claim 6, wherein the at least one allergen inlet is a set of one or several simple openings.

11. An allergen exposure system according to claim 1, wherein the allergen exposure system also includes a filtration device arranged at the at least one air inlet or is interposed between the at least one air inlet and the air inlet duct or is placed in the air inlet duct.

12. An allergen exposure system according to claim 6, wherein the at least one diffusion outlet is provided with a grille for directing or adjusting the flow of air containing the allergen particles.

13. An allergen exposure system according to claim 6, wherein the mixing chamber comprises fins, ribs, walls, baffles or channeling or deviating means, for directing flows inside the mixing chamber.

14. An allergen exposure system according to claim 6, wherein the mixing chamber contains at least one temperature, pressure, or humidity sensor.

15. An allergen exposure system according to claim 6, wherein the walls of the mixing chamber are made of a material which does not release particles or releases few particles.

16. An allergen exposure system according to claim 6, wherein the mixing chamber is situated at least partially above the exposure room.

17. An allergen exposure system according to claim 6, wherein, at an end of the mixing chamber proximate to the diffusion outlet, the section of the mixing chamber decreases to form a narrowing.

18. An allergen exposure system according to claim 6, wherein the at least one diffusion outlet is an opening made in a wall of said walls of the mixing chamber opening out into the exposure room or into an open duct extending from mixing chamber to exposure room.

19. An allergen exposure system according to claim 6, wherein the mixing chamber comprises a gradual narrowing followed by a gradual widening of its width, thus forming a throttle zone in which there is the at least one allergen inlet.

20. An allergen exposure system according to claim 6, wherein air entering the mixing chamber is devoid of allergens other than allergens deliberately introduced through the at least one allergen inlet.

* * * * *

UNITED STATES PATENT AND TRADEMARK OFFICE
CERTIFICATE OF CORRECTION

PATENT NO. : 10,966,653 B2  
APPLICATION NO. : 15/120407  
DATED : April 6, 2021  
INVENTOR(S) : Santailler Page 1 of 1

It is certified that error appears in the above-identified patent and that said Letters Patent is hereby corrected as shown below:

In the Claims

At Column 12, Line 16, "claim 1," should be -- claim 6, --.

Signed and Sealed this  
Twenty-first Day of December, 2021

Drew Hirshfeld  
*Performing the Functions and Duties of the*  
*Under Secretary of Commerce for Intellectual Property and*  
*Director of the United States Patent and Trademark Office*